United States Patent [19]

Vijayalakshmi et al.

[11] Patent Number: 4,666,604

[45] Date of Patent: May 19, 1987

[54] NEW ELUTION COMPLEX MORE ESPECIALLY FOR AFFINITY CHROMATOGRAPHY AND AFFINITY PRECIPITATION

[75] Inventors: Mookambeswaran A. Vijayalakshmi; Sunanda Rajgopal, both of Compiegne, France

[73] Assignee: Centre National de la Recherche Scientifique, Paris, France

[21] Appl. No.: 780,126

[22] Filed: Sep. 25, 1985

[30] Foreign Application Priority Data

Sep. 26, 1984 [FR] France ................. 84 14786

[51] Int. Cl.$^4$ ............................................. B01D 15/08
[52] U.S. Cl. ..................... 210/542; 210/635; 210/656; 210/672; 210/674; 210/500.1; 210/502.1; 252/1; 252/364
[58] Field of Search ............ 210/635, 656, 198.2, 210/672, 674, 500.1, 502.1, 542; 252/1, 364

[56] References Cited

U.S. PATENT DOCUMENTS 4,409,335  10/1983  Hanamoto et al. ............... 210/656

FOREIGN PATENT DOCUMENTS 0064833  11/1982  European Pat. Off. ............ 210/656
0064378  11/1982  European Pat. Off. ............ 210/656

OTHER PUBLICATIONS

Small et al., High–Performance Liquid Affinity Chromatography Of Enzymes On Silica–Immobilised Triazine Dyes; J. Of Chrom. 261 (1981) 175–190.

Dyes–A Colourful Addition To Protein Purification By Yvonne Hey And Peter D. G. Dean; Chemistry & Industry, Oct. 17, 1981.

Primary Examiner—Ernest G. Therkorn
Attorney, Agent, or Firm—Armstrong, Nikaido, Marmelstein & Kubovcik

[57] ABSTRACT

A novel elution complex is provided more especially for affinity chromatography and affinity precipitation for recovering in particular luciferase hexokinase and lactate dehydrogenase.

This complex comprises 1 mM to 30 mM of $MgSO_4$, from 30 mM to 50 mM of EDTA, possibly about 5 mM of ribose or mannose and possibly about 1 mM of DTT.

6 Claims, No Drawings

NEW ELUTION COMPLEX MORE ESPECIALLY FOR AFFINITY CHROMATOGRAPHY AND AFFINITY PRECIPITATION

BACKGROUND OF THE INVENTION

The present invention relates to a novel elution complex particularly adapted to affinity chromatography and affinity precipitation.

Affinity chromatography is a technique at present very widely used for isolating enzymes and purifying them so as to obtain the desired enzyme with a high degree of purity. One of the delicate phases of this technique is the elution: the desired enzyme or sometimes an assembly of enzymes must be exclusively entrained. In fact, it has been possible to retain several types of enzymes on the chromatography column. In order to be sure that only the desired enzyme is eluted, a solution is used containing a substrate of this enzyme.

Thus, for example, the hexokinases, which have as substrate nicotinamide-adenine-dinucleotide phosphate (NADP) are eluted by means of a solution containing this compound; similarly, luciferase which has adenosine-triphosphate (ATP) as specific substrate, is eluted by means of a solution containing this acid.

Affinity precipitation is another technique which can be used for isolating enzymes and purifying them. It is closely related to affinity chromatography and immuno precipitation. This technique comprises first precipitating the enzyme to be purified with a dimerized bifunctional ligand and then specifically dissociating said enzyme with a solution containing its specific substrate.

But the substrates, particularly those mentioned above, are sometimes expensive because they are difficult to obtain. In addition, once the enzyme has been removed from the elution solution, the remaining solution cannot be reused and this recycling impossibility further increases the cost price of the enzyme.

Therefore, one of the aims of the present invention is to provide an elution complex more especially for affinity chromatography and affinity precipitation which performs as well as the specific substrate for the enzyme used to elute the enzyme retained on the chromatography column.

An object of the invention is such an elution complex, the production of which is easy and inexpensive, thus allowing enzyme production at as low a cost as possible.

SUMMARY OF THE INVENTION

This aim and this object, as well as others which will appear further on, are attained by means of an elution complex, more especially for affinity chromatography and for affinity precipitation which, in accordance with the present invention, comprises a magnesium salt and ethylene-diamino-tetracetic acid (EDTA) and has a slightly basic pH.

Advantageously, the magnesium salt whose concentration is between 1 mM and 30 mM is magnesium sulphate ($MgSO_4$).

Preferably, the ethylene-diamino-tetracetic acid concentration is between 30 mM and 50 mM.

In a preferred embodiment of the invention, the elution complex also comprises ribose or mannose.

Advantageously, the ribose or mannose concentration in the complex is 5 mM.

Preferably, this complex also comprises dithiothreitol in a concentration of the order of 1 mM.

As was mentioned above, the present invention relates to an elution complex for affinity chromatography and for affinity precipitation which allows an enzyme to be eluted without using the substrate of this enzyme.

The applicant was led to study a simple complex, capable of being produced industrially, with a good shelf life and inexpensive. This complex comprises more particularly magnesium in salt form and ethylenediamino-tetracetic acid (EDTA), to which a sugar such as ribose or mannose may be added, as well as dithiothreitol (DTT). The pH of this complex must be slightly basic: in general it is of the order of 7.4.

More precisely, this complex comprises from 1 mM to 20 mM magnesium ions and from 30 to 50 mM ethylenediamino-tetracetic acid, with possibly about 5 mM of sugar and about 1 mM of dithiothreitol.

The following examples of implementation of the present invention, which have no limitative character, permit a man skilled in the art to better understand the present invention, as well as its advantages.

EXAMPLE 1

Recovery of luciferase by affinity chromatography

Luciferase is an enzyme whose specific substrate is adenosine-triphosphate or A.T.P. This enzyme is isolated by affinity chromatography on a column containing Blue-Sepharose.

The elution for recovering pure luciferase was achieved with several eluents the composition of which is given in the following table I:

TABLE I

| Eluent | 1 | 2 | 3 | 4 | 5 |
|---|---|---|---|---|---|
| [1]MOPS | 0.01 mM | — | — | — | — |
| ATP | 0.5 mM | — | — | — | — |
| EDTA | — | 30 mM | 40 mM | 40 mM | 40 mM |
| [2]$Mg^{++}$ | 20 mM | 20 mM | 20 mM | 20 mM | 20mM |
| Ribose | — | — | — | 5 mM | — |
| Mannose | — | — | — | — | 5 mM |
| Glucose | — | — | 5 mM | — | — |
| DTT | 1 mM | — | 1 mM | 1 mM | 1 mM |

[1]MOPS: 3 (N—morpholino)-propane sulfonic acid
[2]in the form of magnesium sulphate $MgSO_4$ In the table II below are shown the results of the elution achieved with the eluents mentioned in table I.

TABLE II

| Eluent | pH | % luciferase activity | % of protein recovered | purification multiplication |
|---|---|---|---|---|
| 1 | 7.4 | 180 | 63 | 3.0 |
| 2 | 7.4 | 20 | 70 | — |
| 3 | 7.4 | 0 | Negligible | — |
| 4 | 7.4 | 120 | 58 | 2.0 |
| 5 | 7.4 | 67 | 37 | 1.8 |

It is then apparent that a complex comprising a magnesium salt and ethylene-diamino-tetracetic acid (EDTA) and possibly a sugar which cannot be glucose, but ribose or mannose, as well as dithiothreitol is able to advantageously replace ATP for eluting luciferase. Thus, eluents 2, 4 or 5 are satisfactory, eluents 4 giving the best performances.

EXAMPLE 2

Recovery of hexokinase by affinity chromatography

Hexokinase is an enzyme whose specific substrate is nicotinamide-adenine-dinucleotide phosphate or NADP. This enzyme is isolated, by affinity chromatography on a column of Sepharose 4B linked with Procion Blue HB.

The eluent for recovering the pure hexokinase retained on such a column is usually a solution of NADP. In accordance with the invention, the applicant has shown that a complex comprising 5 mM of a magnesium salt such as magnesium sulphate (MgSO$_4$), and 40 mM of EDTA, to which 5 mM of ribose are added, is perfectly suitable for recovering all the hexokinase retained by such a column. The pH of this complex is of the order of 7.4.

EXAMPLE 3

Recovery of lactate dehydrogenase by affinity chromatography

Lactate dehydrogenase is an enzyme whose specific substrate is NAD+ (nicotinamide-adenine-dinucleotide). This enzyme is isolated by affinity chromatography on a column of Sepharose 4B coupled to Procion Blue HB.

The eluent for recovering the pure lactate dehydrogenase retained on such a column is usually a solution of NAD+ and pyruvate. According to the invention, the applicant has shown that a complex comprising 20 mM of a magnesium salt such as magnesium sulphate (MgSO$_4$) and 40 mM of EDTA to which 5 mM of ribose are added, with or without addition of pyruvate, is perfectly suitable for recovering all the lactate dehydrogenase retained by such a column. The pH of this complex is of the order of 7.5.

EXAMPLE 4

Recovery of lactate dehydrogenase lactate by affinity precipitation

This enzyme is precipitated with the Cibacron dimer.

The eluent recovering most (90%) of the pure lactate dehydrogenase precipitated is usually a solution of NaD+ and pyruvate. According to the invention the applicant has shown that a complex comprising 20 to 30 mM of a magnesium salt such as magnesium sulfate (MgSO$_4$) and 40 mM of EDTA to which 5 mM of ribose are added, with or without addition of pyruvate, is perfectly suitable for recovering the same quantity (90%) of the enzyme. The pH of this complex is of the order of 7.5.

We claim:

1. An elution complex for affinity chromatography and affinity precipitation comprising a magnesium salt, ethylene-diamino-tetracetic acid (EDTA), and ribose or mannose, and having a slightly basic pH.

2. The complex according to claim 1, further comprising dithiothreitol.

3. The complex according to claim 2, wherein the dithiothreitol concentration is of the order of 1 mM.

4. The complex according to claim 2 comprising 20 mM of magnesium sulphate, 40 mM of EDTA, 5 mM of ribose and 1 mM of dithiothreitol.

5. The complex according to claim 1, wherein the ribose or mannose concentration is of the order of 5 mM.

6. The complex according to claim 1 comprising 5 mM of magnesium sulphate, 40 mM of EDTA and 5 mM of ribose.

* * * * *